United States Patent [19]

Cannon

[11] Patent Number: 4,613,620
[45] Date of Patent: Sep. 23, 1986

[54] NOVEL OXIODINIUM AND THIAIODINIUM COMPOUNDS

[75] Inventor: William N. Cannon, Greenwood, Ind.

[73] Assignee: Eli Lilly and Company, Indianapolis, Ind.

[21] Appl. No.: 234,238

[22] Filed: Feb. 13, 1981

Related U.S. Application Data

[60] Division of Ser. No. 41,283, May 21, 1979, Pat. No. 4,283,349, which is a division of Ser. No. 337,345, Mar. 2, 1973, Pat. No. 4,193,935, which is a continuation-in-part of Ser. No. 16,589, Mar. 4, 1970, abandoned, which is a continuation-in-part of Ser. No. 654,656, Jul. 19, 1967, Pat. No. 3,506,719, which is a continuation-in-part of Ser. No. 270,545, Apr. 4, 1963, abandoned.

[51] Int. Cl.[4] .............................................. A01N 37/00
[52] U.S. Cl. .................................... 514/570; 514/557; 514/568; 514/574; 514/576
[58] Field of Search ................ 424/315, 317; 514/557, 514/568, 570, 574, 576

[56] References Cited

U.S. PATENT DOCUMENTS 3,244,636  4/1966  Reller et al. .................... 260/505 R Primary Examiner—Alan Siegel
Attorney, Agent, or Firm—James L. Rowe; Charles W. Ashbrook; Leroy Whitaker

[57] ABSTRACT

Novel oxiodinium and thiaiodinium compounds having a superior inhibitory effect against micro-organisms coupled with outstanding stability and low toxicity are described.

1 Claim, No Drawings

NOVEL OXIODINIUM AND THIAIODINIUM COMPOUNDS

CROSS-REFERENCE

This application is a division of application Ser. No. 41,283, filed May 21, 1979 now U.S. Pat. No. 4,283,349, which was a division of application Ser. No. 337,345, filed Mar. 2, 1973, now U.S. Pat. No. 4,193,935, which was a continuation-in-part of application Ser. No. 16,589, filed Mar. 4, 1970, now abandoned, which application was a continuation-in-part of application Ser. No. 654,656, filed July 19, 1967, now U.S. Pat. No. 3,506,719, which application was a continuation-in-part of application Ser. No. 270,545, filed Apr. 4, 1963, now abandoned.

BACKGROUND OF THE INVENTION

Trivalent iodine compounds in which the iodine atom is attached to two aromatic rings to form an iodonium cation have been known for a number of years. (See for example Masson and Race, *J. Chem. Soc.* 1937 1716, and U.S. Pat. No. 2,878,293.) Beginning in 1947, Sandin and co-workers reinvestigated the preparation of dibenziodolium iodides which differ from the iodonium compounds of Masson in that the two phenyl rings are directly bonded. The original preparation of a dibenziodolium compound was published in 1908 by Mascarelli and Benati, *Gazz. chim. ital.* 38 624 (1908), but this work was apparently overlooked by Masson and Race. The Sandin work is contained in the following papers: Wasylewsky, Brown and Sandin, *J. Am. Chem. Soc.* 72, 1039 (1950) and Collette et al., *J. Am. Chem. Soc.* 78, 3819 (1956). The use of dibenziodolium compounds as bactericides is disclosed in U.S. Pat. No. 3,207,660 as well as in Australian Pat. No. 21749/62 and South African Pat. No. 63/4106 1964 (Derwent Farm. Doc. nos. 11012 and 12453). Certain extremely powerful microbiocidal halogen-substituted dibenziodolium salts are disclosed in U.S. Pat. No. 3,264,355. An excellent review of the chemistry of heterocyclic iodine compounds is contained in a review by Banks "Organic Polyvalent Iodine Compounds," *Chemical Review* 16, 243 (1966).

Heterocyclic iodine compounds in which the two phenyl rings are joined other than by a direct bond or by an alkyl group have not heretofore been known with one exception, an oxygen-bridged compound, 3,7-dinitrodibenz[be][1,4]oxiodinium iodide, was prepared by Hwang et al., *K'o Hsueh T'ung Pao* No. 2, 49–50 (1957), abstracted in *Chemical Abstracts* 53, 4280 (1959). Hwang et al. also stated that they were unable to prepare the corresponding thiaiodinium compound.

SUMMARY

The compounds provided by this invention can be represented by the following formula:

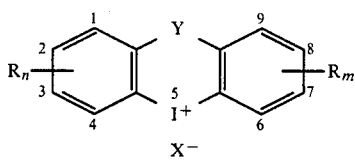

wherein
Y is oxygen or sulfur;
R is lower alkyl, trifluoromethyl or halo;
n and m are numbers from 0 to 3, and;
$X^-$ is an anion selected from the group consisting of $C_1$–$C_{10}$ alkanoates, benzoate, substituted benzoate, benzenesulfonate, substituted benzenesulfonate, fumarate, phenate, citrate, lactate, tartrate, phenylacetate, and $C_1$–$C_3$ alkylsulfonates.

Compounds represented by the above formula when Y is oxygen are denominated generically as dibenz[be][1,4]oxiodinium compounds and when Y is sulfur as dibenz[be][1,4]thiaiodinium compounds.

In the above formula, when R represents $C_1$–$C_3$ alkyl group, it can be methyl, ethyl, n-propyl, isopropyl, and the like. Suitable substituents for substituted benzoate or benzenesulfonate include chloro, bromo, iodo, nitro, $C_1$–$C_3$ alkyl, $C_1$–$C_3$ alkoxy, hydroxy and the like. Anions represented by $X^-$ include the following $C_1$–$C_{10}$ alkanoates: formate, acetate, propionate, butyrate, valerate, caproate, enanthate, caprylate, pelargonate, caprate; the following benzoates, chlorobenzoate, methylbenzoate, dinitrobenzoate, hydroxybenzoate, methoxybenzoate, and the following benzene sulfonates or $C_1$–$C_3$ alkylsulfonates: toluenesulfonate, methanesulfonate, ethanesulfonate, propanesulfonate, methoxybenzenesulfonate, and chlorobenzenesulfonate.

Representative compounds coming within the scope of the above formula include the following:
4-chlorodibenz[be][1,4]oxiodinium acetate
2,4-dichlorobenz[be][1,4]oxiodinium lactate
3,7-dibromodibenz[be][1,4]oxiodinium tartrate
2,8-ditrifluoromethyldibenz[be][1,4]oxiodinium methanesulfonate
4-n-propyldibenz[be][1,4]thiaiodinium sulfonate citrate
4,6-difluorodibenz[be][1,4]thiaiodinium ethanesulfonate
bis-(2-ethyldibenz[be][1,4]oxiodinium)phenate
1-chloro-3-methyldibenz[be][1,4]oxiodinium benzoate
3-chloro-9-bromodibenz[be][1,4]oxiodinium tosylate,
and the like.

Of special interest are compounds in which $X^-$ is acetate, propionate, decanoate, benzoate, substituted benzoate phenylacetate, benzenesulfonate, substituted benzenesulfonate, fumarate, lactate, tartrate and citrate. Another group of salts with particularly desirable solubility properties are those in which $X^-$ is $C_1$–$C_3$ alkylsulfonate.

Compounds represented by the above formula can be prepared by tetra-azotizing a suitably substituted 2,2'-diaminodiphenyl oxide or 2,2'-diaminodiphenylsulfide and then decomposing the tetra-azotate in the presence of an iodide salt. A preferable method, however, for the preparation of the above compounds involves the direct iodination of a suitably substituted diphenyl ether or diphenyl sulfide using iodosyl sulfate in sulfuric acid solution as the iodinating reagent. The product of this reaction is usually a dibenz[be][1,4]oxiodinium or thiaiodinium bisulfate. Recrystallization of the bisulfate salt from water usually serves to convert it to the corresponding sulfate salt.

A third method is available for the preparation of compounds represented by the above formula in which Y is oxygen. According to this procedure, a suitably substituted 2-iododiphenyl ether is reacted with peracetic acid to give the corresponding iodoso compound, which can then be cyclized in the presence of concentrated sulfuric acid to yield, usually, the bisulfate salt of the desired oxiodinium compound. Alternatively, the 2-iododiphenyl ether can be chlorinated to yield a 2-dichloriodo compound, which can be hydrolyzed to the corresponding iodoso compound in base and the iodoso compound cyclized as above.

The various salts which are produced in any of the above reactions can be transformed to other salts by standard metathetic processes. For example, a sulfate salt can be dissolved in water and treated with a large excess of sodium acetate to yield the corresponding acetate, or with a large excess of sodium methanesulfonate to yield the corresponding methanesulfonate. Other methods of preparing salts of the oxiodinium or thiaiodinium compounds of this invention will be readily discernable by those skilled in the art.

The compounds provided by this invention inhibit the growth of a wide variety of micro-organisms.

Among the types of micro-organisms whose growth is inhibited by the application to their habitat of a compound represented by the above formula are included bacteria which are pathogenic for animals and plants, saprophytic bacteria, fungi including both pathogenic and nonpathogenic varieties, and material-degrading organisms. Table I which follows sets forth the minimum bacteriostatic or fungistatic concentration, expressed as micrograms per milliliter (parts per million), for a group of compounds which are illustrative of those represented by the above formula, against a representative group of micro-organisms falling within the above classes.

TABLE I

| | Cation | | | | | | |
|---|---|---|---|---|---|---|---|
| | 3-dichlorodibenz[be][1,4]oxiodinium | | | dibenz[be][1,4]oxiodinium | | | |
| | | | | Anion | | | |
| Test Organisms | chloride | methane sulfonate | sulfate (bis) | methane sulfonate | 3,4-dichlorobenzene sulfonate | salicylate | 1-naphthalene acetate |
| Staphylococcus aureus | 3.13 | 6.25 | 6.25 | 3.12 | <10 | 100 | 100 |
| Bacillus subtillis | 1.56 | 1.56 | .78 | .78 | <10 | <10 | <10 |
| Mycobacterium avium | .78 | .78 | .39 | <39 | <10 | <10 | <10 |
| Streptococcus faecalis | 25 | — | — | 50 | 100 | 100 | 100 |
| Lactobacillus casei | 3.13 | — | 12.5 | 50 | <10 | 100 | 100 |
| Leuconostoc citrovorum | 6.25 | 100 | 12.5 | 3.12 | <10 | <10 | <10 |
| Escherichia coli #1 | 3.25 | 100 | 1.56 | 3.12 | <10 | <10 | <10 |
| Escherichia coli #2 | 6.25 | 6.25 | 3.12 | 3.12 | <10 | <10 | <10 |
| Proteus sp. #1 | 6.25 | 3.12 | 1.56 | .78 | <10 | <10 | <10 |
| Proteus sp. #2 | 6.25 | 6.25 | 1.56 | 3.12 | <10 | <10 | <10 |
| Pseudomonas sp. #2 | 25 | 12.5 | 6.25 | 3.12 | <10 | <10 | <10 |
| Pseudomonas sp. #3 | 6.25 | 6.25 | 1.56 | 3.12 | <10 | <10 | <10 |
| Klebsiella-Aerobacter #14 | 6.25 | 6.25 | 3.13 | 3.12 | <10 | <10 | <10 |
| Klebsiella-Aerobacter #15 | 12.5 | 6.25 | 12.5 | 3.12 | <10 | <10 | <10 |
| Salmonella sp. #1 | 12.5 | 6.25 | 6.25 | 3.12 | <10 | <10 | <10 |
| Vibrio metschnikovii | 6.25 | 6.25 | 6.25 | .78 | <10 | <10 | <10 |
| Saccharomyces pastorianus | 3.13 | 6.25 | 12.5 | 3.12 | <10 | <10 | <10 |
| Candida albicans | 3.13 | 6.25 | .39 | <.39 | <10 | <10 | <10 |
| Trichophyton mentagrophytes | 1.56 | 1.56 | 3.13 | 3.12 | <10 | <10 | <10 |

| | Cation | | | | | |
|---|---|---|---|---|---|---|
| | dibenz[be][1,4]oxiodinium | | | 3,7-dichloro-dibenz[be][1,4]oxiodinium(bis) | | 3,7-dimethyl-dibenz[be][1,4]oxiodinium |
| | | | | Anion | | |
| Test Organisms | benzoate benzoate | naphthalene sulfonate | lactate | sulfate (bis) | methane sulfonate | chloride |
| Staphylococcus aureus | 100 | 100 | <10 | 1.56 | 10 | 6.25 |
| Bacillus subtillis | <10 | <10 | <10 | 1.56 | 10 | 1.56 |
| Mycobacterium avium | <10 | <10 | <10 | .39 | 10 | .39 |
| Streptococcus faecalis | 100 | 100 | <10 | 25 | 100 | 100 |
| Lactobacillus casei | 100 | 100 | <10 | 6.25 | 100 | 6.25 |
| Leuconostoc citrovorum | <10 | <10 | <10 | 3.12 | 10 | 12.5 |
| Escherichia coli #1 | <10 | <10 | <10 | 1.56 | 10 | 6.25 |
| Escherichia coli #2 | <10 | <10 | <10 | 3.12 | 10 | 12.5 |
| Proteus sp. #1 | <10 | <10 | <10 | 3.12 | 10 | 12.5 |
| Proteus sp. #2 | <10 | <10 | <10 | 3.12 | 10 | 12.5 |
| Pseudomonas sp. #2 | <10 | <10 | <10 | 6.25 | 100 | 50 |
| Pseudomonas sp. #3 | <10 | <10 | <10 | 1.56 | 10 | 6.25 |
| Klebsiella-Aerobacter #14 | <10 | <10 | <10 | 3.12 | 10 | 6.25 |
| Klebsiella-Aerobacter #15 | <10 | <10 | <10 | 6.25 | 10 | 25 |
| Salmonella sp. #1 | <10 | <10 | <10 | 3.13 | 100 | 25 |
| Vibrio metschnikovii | <10 | <10 | <10 | 1.56 | 10 | 6.25 |
| Saccharomyces pastorianus | <10 | <10 | <10 | 12.5 | 10 | 25 |
| Candida albicans | <10 | <10 | <10 | 6.25 | 10 | 6.25 |
| Trichophyton mentagrophytes | <10 | <10 | <10 | 1.56 | 10 | 1.56 |

TABLE II

| | Cation | | | | |
|---|---|---|---|---|---|
| | 3-dichlorodibenz[be][1,4]oxiodinium | | dibenz[be][1,4]oxiodinium | | |
| | | | Anion | | |
| | methane | sulfate | methane | 3,4-dichlorobenzene | 1-naphthalene |

TABLE II-continued

| Test Organisms | chloride | sulfonate | (bis) sulfonate | sulfonate | salicylate | acetate |
|---|---|---|---|---|---|---|
| *Agrobacterium tumefaciens* | 12.5 | 6.25 | 6.25 | 3.12 | <10 | <10 | <10 |
| *Erwinia amylovora* | 6.25 | 3.12 | 3.13 | .78 | <10 | <10 | <10 |
| *Pseudomonas solanacearum* | 12.5 | 6.25 | .39 | .78 | <10 | <10 | <10 |
| *Xanthomonas phaseoli* | 6.25 | .78 | .78 | .78 | <10 | <10 | <10 |
| *Alternaria solani* | 12.5 | 6.25 | 1.56 | 3.12 | <10 | <10 | <10 |
| *Aspergillus niger* | 50. | 50. | 12.5 | 50. | 100 | <10 | <10 |
| *Botrytis cinerea* | 3.13 | .78 | 1.56 | <.39 | <10 | <10 | <10 |
| *Ceratostomella ulmi* | 3.13 | 3.13 | .78 | <.39 | <10 | <10 | <10 |
| *Cladosporium Resinae* | — | 6.25 | — | 3.12 | <10 | <10 | <10 |
| *Collectotrichum pisi* | 12.5 | 6.25 | 6.25 | 12.5 | <10 | <10 | <10 |
| *Fusarium oxysporum* | 25. | 3.12 | 3.13 | 3.12 | <10 | <10 | <10 |
| *Glomerella cingulate* | 12.5 | 6.25 | 6.25 | 3.12 | 100 | <10 | <10 |
| *Helminthosporium sativum* | 12.5 | 6.25 | 3.13 | <.39 | <10 | <10 | <10 |
| *Penicillium expansum* | 25. | 12.5 | 6.25 | 3.12 | <10 | <10 | <10 |
| Pullularia sp. | 25. | 50. | 3.13 | 3.12 | <10 | <10 | <10 |
| *Sclerotinia fructicola* | 25. | 6.25 | .78 | 3.12 | <10 | <10 | <10 |
| *Verticillium albo-atrum* | 100.5 | 25. | 12.5 | 12.5 | <10 | <10 | <10 |
| *Mucor ramannianus* | 25. | 12.5 | 12.5 | 3.12 | <10 | <10 | <10 |
| *Spicaria divaricata* | 25. | 1.56 | 6.25 | <.39 | <10 | <10 | <10 |

| | Cation | | | |
|---|---|---|---|---|
| | dibenz[be][1,4]oxiodinium | 3,7-dichloro-dibenz[be][1,4]oxiodinium(bis) | 3,7-dimethyl-dibenz[be][1,4]oxiodinium | |
| | Anion | | | | |
| Test Organisms | benzoyl-benzoate | naphthalene sulfonate | lactate | sulfate (bis) | methane sulfonate | chloride |
|---|---|---|---|---|---|---|
| *Agrobacterium tumefaciens* | <10 | <10 | <10 | 6.25 | <10 | 25. |
| *Erwinia amylovora* | <10 | <10 | <10 | 3.13 | <10 | 12.5 |
| *Pseudomonas solanacearum* | <10 | <10 | <10 | .39 | <10 | — |
| *Xanthomonas phaseoli* | <10 | <10 | <10 | .78 | <10 | 6.25 |
| *Alternaria solani* | <10 | <10 | <10 | 100 | 25. | |
| *Aspergillus niger* | <10 | 100 | <10 | 12.5 | <10 | 50. |
| *Botrytis cinerea* | <10 | <10 | <10 | 1.56 | <10 | — |
| *Ceratostomella ulmi* | <10 | <10 | <10 | 1.56 | <10 | 1.56 |
| *Cladosporium Resinae* | <10 | <10 | <10 | 6.25 | <10 | 12.5 |
| *Collectotrichum pisi* | <10 | <10 | <10 | 3.12 | <10 | 6.25 |
| *Fusarium oxysporum* | <10 | <10 | <10 | 6.25 | <10 | 25 |
| *Glomerella cingulate* | <10 | 100 | <10 | 6.25 | <10 | 12.5 |
| *Helminthosporium sativum* | <10 | <10 | <10 | 3.12 | <10 | 12.5 |
| *Penicillium expansum* | <10 | <10 | <10 | 6.25 | <10 | 12.5 |
| Pullularia sp. | <10 | <10 | <10 | 6.25 | <10 | 25. |
| *Sclerotinia fructicola* | <10 | <10 | <10 | 3.12 | <10 | 25. |
| *Verticillium albo-atrum* | <10 | 100 | <10 | 12.5 | <10 | 25. |
| *Mucor ramannianus* | <10 | <10 | <10 | 12.5 | <10 | 12.5 |
| *Spicaria divaricata* | <10 | <10 | <10 | 3.12 | <10 | 6.25 |

In addition to their activity against the micro-organisms listed in Table I, the compounds of this invention also show activity against various species of algae, including for example: *Bracteococcus cinnabarinus, Chlorella vulgaris, Scenedesmus naegili, Stichococcus bacillaris, Chlorocloster engadinesis,* Trebouxia sp., and *Scenedesmus basiliensis.* The compounds also show activity against other material-degrading organisms, than those listed in Table I, e.g., *Chaetomium globosum, Myrothecium verricaria, Aspergillus ustus, Aspergillus clavatus,* and *Penicillium commune.*

It is apparent from the antibacterial, antifungal, and antimildew activity demonstrated by the cationic salts of this invention, as set forth above, that they can be used as preservatives, disinfectants, and the like, in ways that antibacterial and antifungal agents have been used in the past. For example, a bacteriostatic or fungistatic amount of a salt represented by the above formula can be added to paints, ointments lotions, and foods to prevent the growth of micro-organisms therein. In addition, the salts of this invention can be employed in solution to disinfect glassware, hospital walls, and similar areas. The compounds can also be employed in embalming fluids in conjunction with formaldehyde or other known embalming agents. Further, they can be used in the form of dusts, solutions, wettable powders, emulsions, and the like on various agricultural and garden plants to prevent the growth thereon of various pathogenic organisms.

In addition to the above uses as antimicrobial agents, the salts of this invention can also be employed as pesticides. For example, they inhibit the growth of certain higher organisms such as protozoa, nematodes, etc. In somewhat higher concentrations than those required to inhibit microbial growth, they can be employed to kill various types of vermin and, in concentrations greatly in excess of those which prevent the growth of mildew on roses, for example, certain of the compounds will act as defoliants or in some instances as herbicides.

Surprisingly, the compounds of this invention are far more stable than the 3,7-dinitrodibenz[be][1,4]iodolium iodide of the prior art. For example, the prior art compound loses its antiseptic effectiveness in 0.10 percent solution after 72 hours at pH 9, and at room temperature, whereas a 0.10 percent solution of 3-chlorodibenz-[be][1,4]oxiodinium methane sulfonate is still approximately 100 percent effective after two weeks at room temperature or at 37° C. at pH 8 to 10. Other compounds of this invention are correspondingly stable.

This invention is further illustrated by the following specific examples:

EXAMPLE I

Bis-(dibenz[be][1,4]oxiodinium)sulfate

A solution of peracetic acid was freshly prepared according to the procedure of Collette et al. *J. Am. Chem. Soc.*, 78, 3819 (1956). Two hundred fifty milliliters of the solution were placed in a round bottom flask equipped with both stirring and cooling means. The solution was stirred while a second solution containing 48 g. of 2-iododiphenyl ether in 100 ml. of acetic anhydride was added in dropwise fashion. Stirring was continued at ambient room temperature for about 14 hours. The reaction mixture was then cooled to about 0° C., and 15 ml. of 18M sulfuric acid were added thereto in dropwise fashion. The temperature of the reaction was maintained below about 15° C. during the addition. The reaction mixture was then allowed to warm up to ambient room temperature and was stirred at this temperature for about 5.5 hours. It was then poured over about 100 g. of crushed ice. A brownish solid comprising dibenz[be][1,4]oxiodinium bisulfate separated. The solid was collected and twice recrystallized from a minimal amount of hot water to yield bis-(dibenz[be][1,4]oxiodinium)sulfate which melted with decomposition at about 250°–252° C. (The recrystallization procedure served to convert the bisulfate salt which was the original product of the reaction to the sulfate salt.) Analysis-Calc.: C, 42.00; H, 2.35; I, 36.98; S, 4.67. Found: C, 41.93; H, 2.57; I, 37.13; S, 4.61.

The aqueous filtrate from the initial filtration of dibenz[be][1,4]oxiodinium bisulfate was treated with an excess of a saturated sodium chloride solution. An immediate heavy white precipitate was formed. This precipitate was collected by filtration and consisted of dibenz[be][1,4]oxiodinium chloride. The compound melted with decomposition at about 153°–154° C. after recrystallization from a large volume of hot water.

The following compounds were prepared by the method of Example I.

Bis-(3,7-dichlorodibenz[be][1,4]oxiodinium)sulfate
  M.P.=250°–252° C. (with decomposition) Analysis-Calc.: C, 34.94; H, 1.46; I, 30.80; S, 3.89; Cl, 17.20. Found: C, 34.04; H, 1.92; I, 29.96; S, 3.60; Cl, 16.62.
3,7-Dibromodibenz[be][1,4]oxiodinium chloride
  M.P.=255°–256° C. (with decomposition) Analysis-Calc.: C, 29.51; H, 1.23. Found: C, 29.34; H, 1.36.
3-Chlorodibenz[be][1,4]oxiodinium chloride
  M.P.=242°–243° C. (with decomposition).
2,3-Dichlorodibenz[be][1,4]oxiodinium chloride
  M.P.=250°–252° C. (with decomposition).
1-Chlorodibenz[be][1,4]oxiodinium chloride
  M.P.=226°–228° C. (with decomposition).
3-Trifluoromethyldibenz[be][1,4]oxiodinium bisulfate
  M.P.=251°–252° C.
1,3-Dichlorodibenz[be][1,4]oxiodinium chloride
  M.P.=125°–128° C. (with decomposition).
3,7-Dimethyldibenz[be][1,4]oxiodinium chloride
  M.P.=239°–240° C. Analysis-Calc.: I, 35.39; C, 46.89; H, 3.37. Found: I, 35.26; C, 47.38; H, 3.56.
2-Chlorodibenz[be][1,4]oxiodinium chloride
  M.P.=242°–244° C. (with decomposition).

EXAMPLE II

Dibenz[be][1,4]oxiodinium phosphate

A solution of 74 g. of 2-iododiphenyl ether in 75 ml. of chloroform was cooled to about 5° C. and was maintained at about that temperature with stirring while chlorine gas was introduced just above the surface of the solution. A yellow crystalline precipitate of 2-dichloriododiphenyl ether was formed and precipitated. About 300 ml. of hexane were added to the solution, and stirring was continued for about 5 minutes. The dichloriodo compound was separated by filtration, washed with hexane, and dried in air. About 83 g. of 2-dichloriododiphenyl ether were obtained, melting at about 70°–72° C.

Since the compound was somewhat unstable, it was converted immediately into the corresponding iodoso compound as follows:

Two hundred grams of 2-dichloriododiphenyl ether were suspended with stirring in 300 ml. of water and the mixture cooled to about 10° C. Two hundred forty milliliters of 5N sodium hydroxide solution were added in dropwise fashion. The solution was allowed to warm to room temperature and to stand while being stirred for about twelve hours during which time the dichloriodo compound was hydrolyzed to the corresponding iodoso compound. The iodoso compound was separated by filtration and washed with water until the washings were no longer alkaline. 2-Iodosodiphenyl ether thus prepared weighed about 157 g. and melted at about 70°–72° C.

One hundred fifty grams of 2-iodosodiphenyl ether were added in small portions with stirring to 250 ml. of 85 percent phosphoric acid while maintaining the mixture at about room temperature. After the addition of the iodoso compound had been completed, stirring was continued for about eighteen hours. The mixture was then cooled to about 0° C. and filtered. The resulting precipitate was washed free from phosphoric acid with a small amount of cold acetone. The white crystalline solid comprising dibenz[be][1,4]oxiodinium phosphate weighed about 144 g.

EXAMPLE III

Bis-(dibenz[be][1,4]oxiodinium)salts

An aqueous solution containing 5 g. of bis-(dibenz[be][1,4]oxiodinium)sulfate in 500 ml. of water was passed over an anion exchange resin in the OH⁻ form. The effluent from the column was highly alkaline, indicating that the sulfate anions were being removed by the resin and that an aqueous solution of dibenz[be][1,4]oxiodinium hydroxide was coming off the column. After 500 ml. of solution had been passed through the column, the resin was washed with 250 ml. of deionized water. The wash was combined with the effluent, giving a total volume of 750 ml. Acetic acid was added in dropwise fashion with stirring to an aliquot of this solution (which had a pH=13.0) until a pH=5 had been attained. The water was removed from the resulting clear solution in vacuo. The residue comprising dibenz[be][1,4]oxiodinium acetate was dissolved in a minimal amount of anhydrous ethanol. Addition of ether was added to the resulting solution caused dibenz[be][1,4]oxiodinium acetate to precipitate. The salt was a white crystalline solid melting with decomposition at about 160° C.

Following the above procedure, dibenz[be][1,4]-oxiodinium phenate, a cream colored solid melting at about 113°–115° C., was prepared. Other salts prepared in the same fashion include: dibenz[be][1,4]oxiodinium lactate melting at about 122° C. with decomposition; dibenz[be][1,4]oxiodinium benzoate melting at about 108°–110° C.; 3-chlorodibenz[be][1,4]oxiodinium methanesulfonate melting at about 207°-209° C.; 3,7-dichlorodibenz[be][1,4]oxiodinium lactate melting at about 227°-228° C.; 3,7-dimethyldibenz[be][1,4]oxiodinium methanesulfonate melting at about 195°-196° C. and the following salts of the dibenz[be][1,4]oxiodinium cation: salicylate M.P.=180°-182° C.; 1-naphthalenacetate M.P.=180°-181° C.; 2-benzoylbenzoate M.P.=175°-176° C.; 2-naphthalenesulfonate M.P.=222°-224° C.; 3,4-dichlorobenzenesulfonate M.P.=210°-212° C.; dihydrogenphosphate M.P.=245°-246° C.; methanesulfonate M.P.=220°-223° C.; and 3-chlorodibenz[be][1,4]oxiodinium methanesulfonate M.P.=207°-209° C.

Salts of the oxiodinium cations coming within the scope of formula I can be prepared by substituting the corresponding acid for acetic acid in the above example while using the appropriate oxiodinium sulfate or bisulfate as a source of the cation.

I claim:

1. A method of inhibiting the growth of micro-organisms which comprises applying to a micro-organism habitat an effective amount of a compound represented by the following formula:

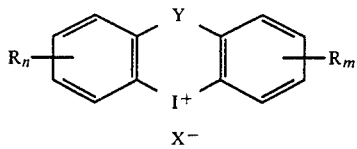

wherein
Y is oxygen or sulfur;
R is lower alkyl, trifluoromethyl or halo;
n and m are numbers of 0 to 3; and
$X^-$ is an anion selected from the group consisting of acetate, propionate, benzoate, benzenesulfonate, fumarate, citrate, lactate, tartrate, and phenylacetate.

* * * * *